(12) United States Patent
Kimoto

(10) Patent No.: US 7,931,585 B2
(45) Date of Patent: Apr. 26, 2011

(54) TRANSMITTING APPARATUS, RECEIVING APPARATUS, AND BODY-INSERTABLE APPARATUS SYSTEM

(75) Inventor: Seiichiro Kimoto, Tokyo (JP)

(73) Assignee: Olympus Corporation, Tokyo (JP)

( * ) Notice: Subject to any disclaimer, the term of this patent is extended or adjusted under 35 U.S.C. 154(b) by 1184 days.

(21) Appl. No.: 11/595,051

(22) Filed: Nov. 9, 2006

(65) Prior Publication Data
US 2007/0055099 A1    Mar. 8, 2007

Related U.S. Application Data

(63) Continuation of application No. PCT/JP2005/008534, filed on Mar. 10, 2005.

(30) Foreign Application Priority Data

May 10, 2004  (JP) .................................. 2004-139891
Sep. 9, 2004  (JP) .................................. 2004-263003

(51) Int. Cl.
*A61B 1/04* (2006.01)
*H04N 7/00* (2006.01)

(52) U.S. Cl. .......................... 600/109; 600/118; 348/476

(58) Field of Classification Search .................. 600/118, 600/109, 302; 455/130; 375/316; 348/473, 348/476, 479
See application file for complete search history.

(56) References Cited

U.S. PATENT DOCUMENTS

| | | | | |
|---|---|---|---|---|
| 3,896,487 A | * | 7/1975 | Tesler | 348/43 |
| 4,599,654 A | * | 7/1986 | Monroe | 348/363 |
| 4,896,213 A | * | 1/1990 | Kobo et al. | 348/478 |
| 4,970,592 A | * | 11/1990 | Becker et al. | 348/496 |
| 5,040,063 A | * | 8/1991 | Citta et al. | 348/470 |
| 5,142,643 A | * | 8/1992 | Yonejirou et al. | 348/692 |
| 5,604,531 A | | 2/1997 | Iddan et al. | |
| 6,356,302 B1 | * | 3/2002 | Kawakami et al. | 348/193 |
| 7,511,742 B2 | * | 3/2009 | Ito et al. | 348/231.2 |
| 2007/0159526 A1 | * | 7/2007 | Abe | 348/65 |

FOREIGN PATENT DOCUMENTS

| | | |
|---|---|---|
| EP | 0 212 839 | 3/1987 |
| JP | 62-18174 | 1/1987 |
| JP | 62-111578 | 5/1987 |
| JP | 07-030881 | 1/1995 |
| JP | 2001-231186 | 8/2001 |
| JP | 2003-019111 | 1/2003 |

OTHER PUBLICATIONS

Two (2) Japanese Office Actions dated May 22, 2007.

\* cited by examiner

*Primary Examiner* — John P Leubecker
(74) *Attorney, Agent, or Firm* — Scully, Scott, Murphy & Presser, P.C.

(57) ABSTRACT

A transmitting apparatus which externally transmits a radio signal containing at least a main information portion, includes a main information output unit that outputs a signal containing the main information portion; a dummy component output unit that outputs a dummy component including one or more alternating-current signals having a predetermined frequency component; a dummy inserting unit that inserts the dummy component into at least a part of a gap portion in the signal containing the main information portion, the gap portion being a portion where the main information portion does not exist; and a radio transmitting unit that externally transmits the signal which contains the main information portion and the dummy component inserted, by radio.

3 Claims, 16 Drawing Sheets

FIG.11

| REGISTER VALUE | DUMMY SIGNAL PROCESSING | |
|---|---|---|
| 0 | NOT ADD | |
| 1 | IMAGING CLOCK | 1/2 |
| 2 | | 1/4 |
| 3 | | 1/8 |
| 4 | TRANSFER CLOCK | 1/2 |
| 5 | | 1/4 |
| 6 | | 1/8 |
| 7 | ADD ALTERNATELY | |

BLANKING PERIOD | DATA PROCESSING PERIOD

TRANSMITTING APPARATUS, RECEIVING APPARATUS, AND BODY-INSERTABLE APPARATUS SYSTEM

CROSS-REFERENCE TO RELATED APPLICATIONS

This application is a continuation of PCT international application Ser. No. PCT/JP2005/008534 filed Mar. 10, 2005 which designates the United States, incorporated herein by reference, and which claims the benefit of priority from Japanese Patent Applications No. 2004-139891, filed May 10, 2004 and No. 2004-263003, filed Sep. 9, 2004, both incorporated herein by reference.

BACKGROUND OF THE INVENTION

1. Field of the Invention

The present invention relates to a transmitting apparatus that externally transmits a radio signal which contains at least a main information portion, a receiving apparatus that receives the radio signal, and a body-insertable apparatus system.

2. Description of the Related Art

In recent years, a swallowable capsule endoscope is proposed in the field of endoscope. The capsule endoscope is equipped with an imaging function and a radio communication function. The capsule endoscope is swallowed by a subject from a mouth for an observation (examination). After being swallowed, the capsule endoscope moves through inside body cavities, for example, internal organs such as a stomach and a small intestine, following a peristaltic motion inside the subject, and sequentially picks up images inside the body cavities until being naturally discharged.

While moving through the body cavities, the capsule endoscope sequentially transmits data of the picked-up images of the inside to outside by radio communication. The transmitted data is stored in an external memory. After swallowing the capsule endoscope, the subject carries a receiver which has radio communication function and memory function until the capsule endoscope is discharged, and can move freely. After the capsule endoscope is discharged, a doctor or a nurse can retrieve the image data stored in the memory and watch images of the internal organs on a display monitor to make diagnosis (see Japanese Patent Laying-Open No. 2001-231186).

In the conventional capsule endoscope system, the image data picked up by the capsule endoscope is transmitted by radio in a similar data structure to a structure adopted in an NTSC image transmission, for example. Specifically, the conventional capsule endoscope system configures image data which corresponds to one image frame by arranging a horizontal blanking period between data corresponding to a predetermined scanning line and data corresponding to a scanning line adjacent to the predetermined scanning line. The horizontal blanking period is originally provided as a gap which prevents a retrace line from appearing in an image displayed on a cathode ray tube display. The radio signal transmitted from the capsule endoscope has a gap portion corresponding to the horizontal blanking period. The gap portion is made up of a direct-current component which corresponds to logical HIGH or logical LOW in a digital signal.

The conventional capsule endoscope system, however, has a following problem which is attributable to the presence of the gap portion in the radio signal transmitted from the capsule endoscope. The problem caused by the gap portion in the radio signal will be described below in detail.

Firstly, when the conventional capsule endoscope system, which employs the radio signals with the gap portions, uses an AC coupling in a signal processing circuit or the like included in a receiver, instant voltage changes may create problems. A main information portion includes a signal component, which has predetermined amplitude and corresponds to the image data, and an average level of the main information portions corresponds to the signal components. On the other hand, the gap portion has a constant voltage corresponding to logical HIGH or logical LOW. Therefore, the average level of the main information portions generally differs from the average level of the gap portions (i.e., the voltage level corresponding to logical HIGH or logical LOW) by a predetermined amount. The receiver which is to receive the radio signals usually includes an AC coupling circuit including a capacitor and the like in order to reduce an offset that corresponds to the voltage difference.

When the AC coupling circuit as described above is employed in the receiver of the capsule endoscope system, instant voltage changes such as sags can be a problem. When the radio signals are transmitted from the capsule endoscope, voltage changes frequently occur during the reception of image data corresponding to one image frame, since the image data is configured so that the main information portion and the gap portion appear alternately. Then, the AC coupling circuit may have difficulty in following the signal transition, for example.

Further, in the conventional capsule endoscope system, a noise component is difficult to remove from a radio signal received by the receiver at the receiver side. As described above, the gap portion includes a direct-current component of a predetermined voltage level. Therefore, the radio signals transmitted from the capsule endoscope include low frequency components corresponding to the gap portions by a predetermined rate. The horizontal blanking period generally lasts for a few hundred microseconds (μsec) and direct-current signals of a predetermined intensity are output during the horizontal blanking period. Therefore, the radio signals inevitably include low frequency components corresponding to such a time length.

On the other hand, the receiver is usually provided with a frequency filter which serves to extract only the radio signals transmitted from the capsule endoscope by removing the noise components from the received radio signals. The frequency filter has a function of extracting a band of frequency components corresponding to the frequency of the radio signals transmitted from the capsule endoscope. When the radio signals include low frequency components in the gap portions, the frequency filter is required to accommodate a wide band so as to pass the low frequency components of the gap portions. Then, the amount of noise components that can be removed by the frequency filter decreases. Therefore, to make the frequency filter function effectively, the radio signals preferably do not include low frequency components.

SUMMARY OF THE INVENTION

A transmitting apparatus according to one aspect of the present invention externally transmits a radio signal containing at least a main information portion. The transmitting apparatus includes a main information output unit that outputs a signal containing the main information portion; a dummy component output unit that outputs a dummy component including one or more alternating-current signals having a predetermined frequency component; a dummy inserting unit that inserts the dummy component into at least a part of a gap portion in the signal containing the main information portion, the gap portion being a portion where the main information portion does not exist; and a radio transmitting unit that externally transmits the signal which contains the main information portion and the dummy component inserted, by radio.

A body-insertable apparatus system according to another aspect of the present invention includes a body-insertable apparatus that is inserted into a subject to obtain information and that externally transmits a radio signal containing the information obtained; and a receiving apparatus that receives the radio signal transmitted from the body-insertable apparatus. The body-insertable apparatus includes a main information output unit that outputs a signal containing a main information portion that contains obtained in-vivo information; a dummy component output unit that outputs a dummy component including one or more alternating-current signals having a predetermined frequency component; a dummy inserting unit that inserts the dummy component into at least a part of a gap portion in the signal containing the main information portion, the gap portion being a portion where the main information portion does not exist; and a radio transmitting unit that externally transmits the signal which contains the main information portion and the dummy component inserted, by radio. The receiving apparatus includes a receiving antenna; and an external device that receives the radio signal transmitted from the body-insertable apparatus via the receiving antenna to extract the in-vivo information from the received radio signal.

A transmitting apparatus according to still another aspect of the present invention includes a dummy signal adding unit that adds a dummy signal which has an average direct-current level of transmitted signals to a portion of an image signal obtained by imaging, the portion corresponding to at least one of a horizontal blanking period and a vertical blanking period; and a setting unit that sets at least one of whether to add the dummy signal or not and a content of the dummy signal to be added. The dummy signal is added for the blanking period according to a content set by the setting unit.

A receiving apparatus according to still another aspect of the present invention receives an image signal transmitted from a transmitting apparatus, and includes a detecting unit that detects a horizontal blanking period or a vertical blanking period of the image signal; and an adding unit that adds a dummy signal which has an average direct-current level of transmitted signals for the blanking period.

The above and other objects, features, advantages and technical and industrial significance of this invention will be better understood by reading the following detailed description of presently preferred embodiments of the invention, when considered in connection with the accompanying drawings.

BRIEF DESCRIPTION OF THE DRAWINGS

FIG. 11 shows contents stored in a setting register;

DETAILED DESCRIPTION OF THE PREFERRED EMBODIMENTS

A transmitting apparatus, a receiving apparatus, and a body-insertable apparatus system in which the transmitting apparatus and the receiving apparatus are applied to a body-insertable apparatus will be described below as exemplary embodiments (hereinbelow simply referred to as "embodiments") of the present invention. It should be noted that the accompanying drawings are merely schematic, and relation between width and thickness of each portion, thickness ratio of one portion to another, and the like may be different in an actual apparatus and a system. The dimensional relations and the ratio may be different from one drawing to another. Further, it should be noted that though the body-insertable apparatus to which the transmitting apparatus is applied will be described as an example in the following description of the embodiments, the applicable field of the transmitting apparatus should not be interpreted as to be limited to the field of the body-insertable apparatus.

Figure 1:
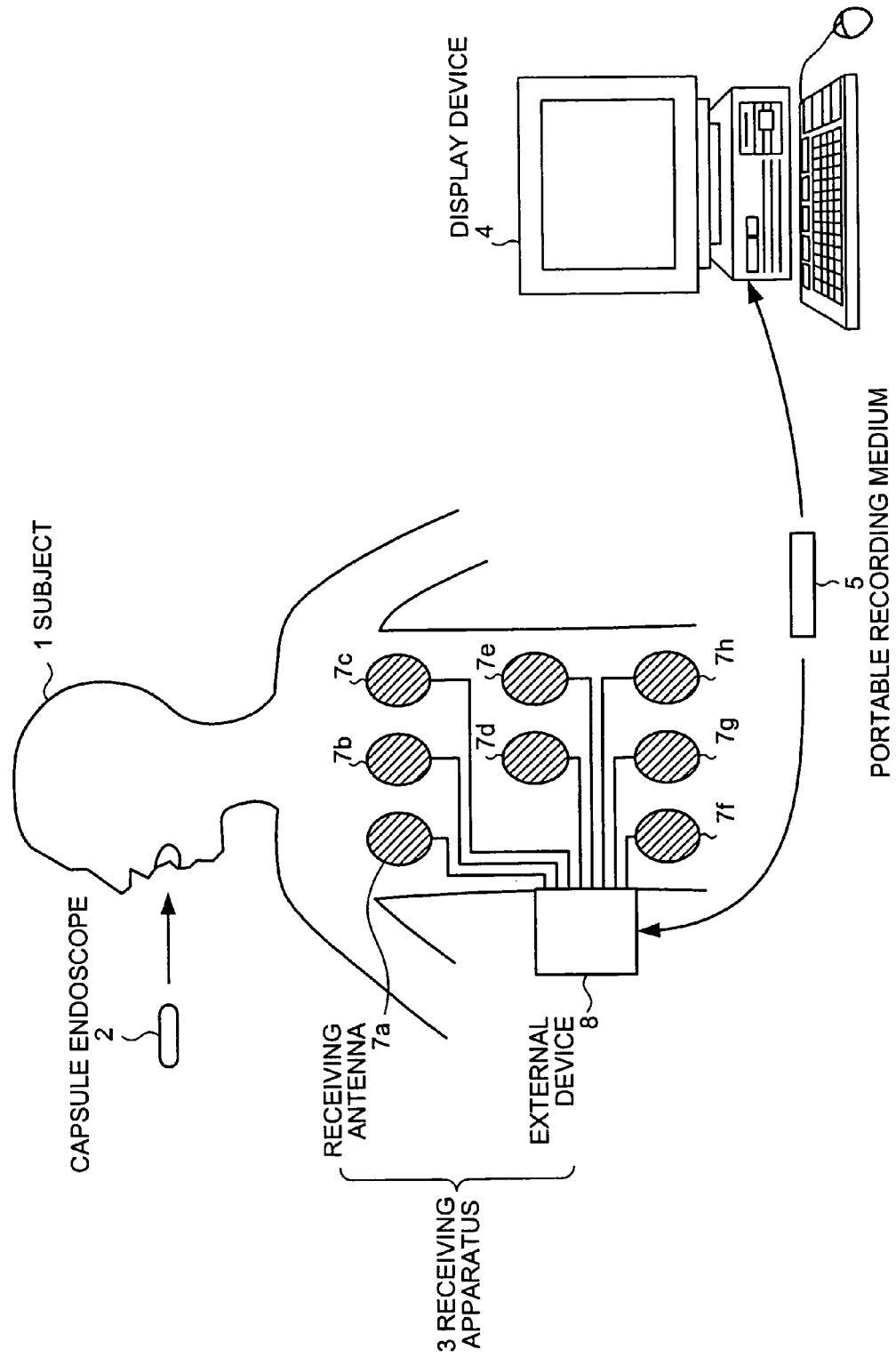
FIG. 1 is a schematic diagram of an overall structure of a body-insertable apparatus system according to a first embodiment.

A body-insertable apparatus system according to a first embodiment will be described. FIG. 1 is a schematic diagram of an overall structure of the body-insertable apparatus system according to the first embodiment. As shown in FIG. 1, the body-insertable apparatus system according to the first embodiment includes a capsule endoscope 2 that is inserted inside a subject 1 and functions as an example of both the transmitting apparatus and the body-insertable apparatus, a receiving apparatus 3 that serves to receive radio signals transmitted from the capsule endoscope 2, a display device 4 that displays contents of the radio signals transmitted from the capsule endoscope 2 and received by the receiving apparatus 3, and a portable recording medium 5 that serves to transfer information between the receiving apparatus 3 and the display device 4.

The display device 4 serves to display an intra-subject image taken by the capsule endoscope 2 and received by the receiving apparatus 3. The display device 4 has a structure as a workstation or the like that displays an image based on data obtained from the portable recording medium 5. Specifically, the display device 4 may directly display an image as in a CRT display, a liquid crystal display, or the like. Alternatively, the display device 4 may output the image onto another media as in a printer.

The portable recording medium 5 can be attached to, and detached from an external device 8 described later and the display device 4. The portable recording medium 5 has such a structure that information can be retrieved therefrom and recorded therein while the portable recording medium 5 is attached to the external device 8 or the display device 4. Specifically, the portable recording medium 5 is attached to the external device 8 while the capsule endoscope 2 moves through the body cavities of the subject 1, and records information related with a position of the capsule endoscope 2. After the capsule endoscope 2 is discharged from the subject 1, the portable recording medium 5 is removed from the external device 8 and attached to the display device 4, and the recorded data is read out by the display device 4. Dissimilar to the system in which the external device 8 and the display device 4 are connected by a cable, the data transfer between the external device 8 and the display device 4 is performed with the use of the portable recording medium 5 such as a compact flash (registered trademark) memory. Therefore, the subject 1 can move freely even while the capsule endoscope 2 moves inside the subject 1.

Figure 2:
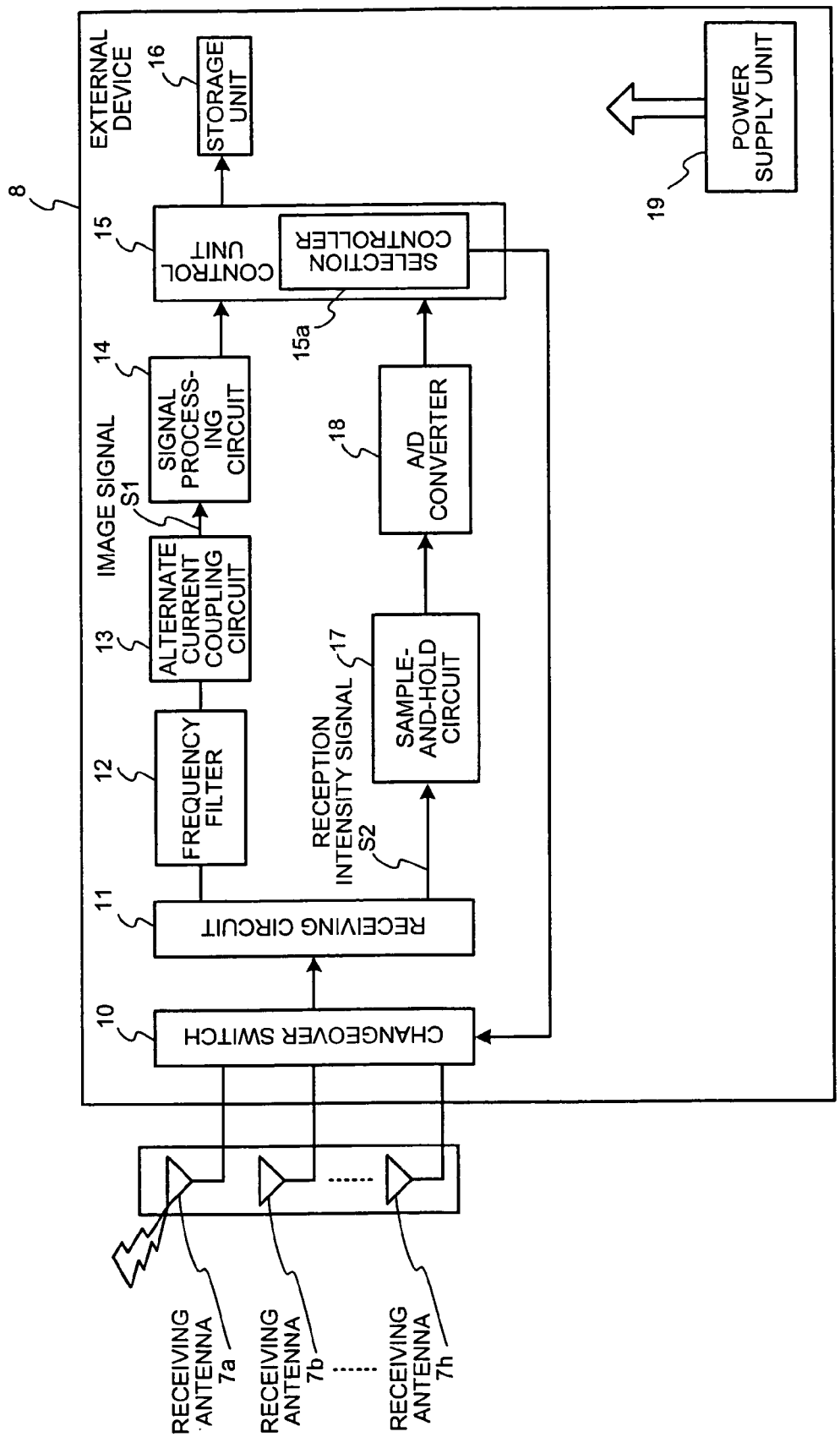
FIG. 2 is a block diagram of a structure of a receiving apparatus included in the body-insertable apparatus system.

The receiving apparatus 3 will be described. FIG. 2 is a schematic block diagram of an overall structure of the receiving apparatus 3. As shown in FIGS. 1 and 2, the receiving apparatus 3 has receiving antennas 7a to 7h that serve to receive the radio signals transmitted from the capsule endoscope 2, and the external device 8 that performs a predetermined process on the radio signals received by the receiving antennas 7a to 7h.

The receiving antennas 7a to 7h serve to receive the radio signals transmitted from the capsule endoscope 2. Specifically, the receiving antennas 7a to 7h each include a loop antenna and a fixing unit for fixing the loop antenna on a body surface of the subject 1, for example. In the first embodiment, the capsule endoscope 2, which sends the radio signals, is inserted into the subject 1 and transmits the radio signal while moving through inside the subject 1. One of the receiving antennas 7a to 7h is selected under the control of the external device 8, and the selected receiving antenna 7 receives the radio signals. Here, a receiving antenna with a most excellent receiving condition of the radio signals, for example, a receiving antenna which receives a signal of a highest intensity may be selected depending on the position of the capsule endoscope 2. Though the number of receiving antennas 7 is eight in the example shown in FIG. 1, the number should not be limited to eight. Any numbers of receiving antennas 7 may be used.

The external device 8 serves to perform a predetermined receiving process on the radio signals received via one of the receiving antennas 7a to 7h. Specifically, the external device 8, as shown in FIG. 2, includes a changeover switch 10 that switches from one of the receiving antennas 7 to another of the receiving antennas 7 to be used for the reception of the radio signals, a receiving circuit 11 that performs a receiving process such as demodulation on the radio signals received via the receiving antenna 7 selected by the changeover switch 10, a frequency filter 12 that performs a filtering on signals output from the receiving circuit, an AC coupling circuit 13 that reproduces a DC (direct-current) component of the filtered signal by AC coupling, a signal processing circuit 14 that performs a predetermined process on an image signal S1 supplied from the AC coupling circuit 13, a control unit 15 that performs an overall control and an output control of the image signal S1 supplied via the signal processing circuit 14, and a storage unit 16 that stores the image signal S1 under the control of the control unit 15. The storage unit 16 has a function of storing the image signal S1 in the portable recording medium 5 shown in FIG. 1.

Further, the external device 8 has a mechanism for selecting an antenna which is suitable for the reception of the radio signals from the receiving antennas 7a to 7h. Specifically, the external device 8 includes a sample-and-hold circuit 17 that samples and holds a received strength signal S2 which indicates an intensity of the radio signal received via the receiving antenna 7, and an A/D converter 18 that converts the received strength signal S2 which is an analog signal output from the sample-and-hold circuit 17 to a digital signal. Further, the control unit 15 includes a selective control unit 15a which performs a controlling operation at the selection of the antenna.

An antenna selecting operation will be briefly described. First, the receiving circuit 11 outputs the received strength signal S2, which is sampled and held by the sample-and-hold circuit 17. The sampled and held signal is converted into a digital signal by the A/D converter 18 and supplied to the selective control unit 15a. An input operation of the received strength signal S2 to the selective control unit 15a is performed for each of the receiving antennas 7a to 7h. The selective control unit 15a selects the receiving antenna 7 whose received strength signal S2 has a highest intensity, and outputs a result of selection to the changeover switch 10. The changeover switch 10 selects the receiving antenna 7 based on the output from the selective control unit 15a. Thereafter, the reception of the radio signals which contains the image signals is performed.

Further, the external device 8 has a power supply unit 19 that serves to supply driving power to each of the components described above. The external device 8 is made up of the components as described hereinabove.

The capsule endoscope 2 will be described. In the first embodiment, the capsule endoscope 2 serves to function as both a transmitting apparatus and a body-insertable apparatus as recited in the appended claims. The capsule endoscope 2 is inserted inside the subject 1, and thereby functions to obtain in-vivo information and to transmit the radio signals to the receiving apparatus 3.

Figure 3:
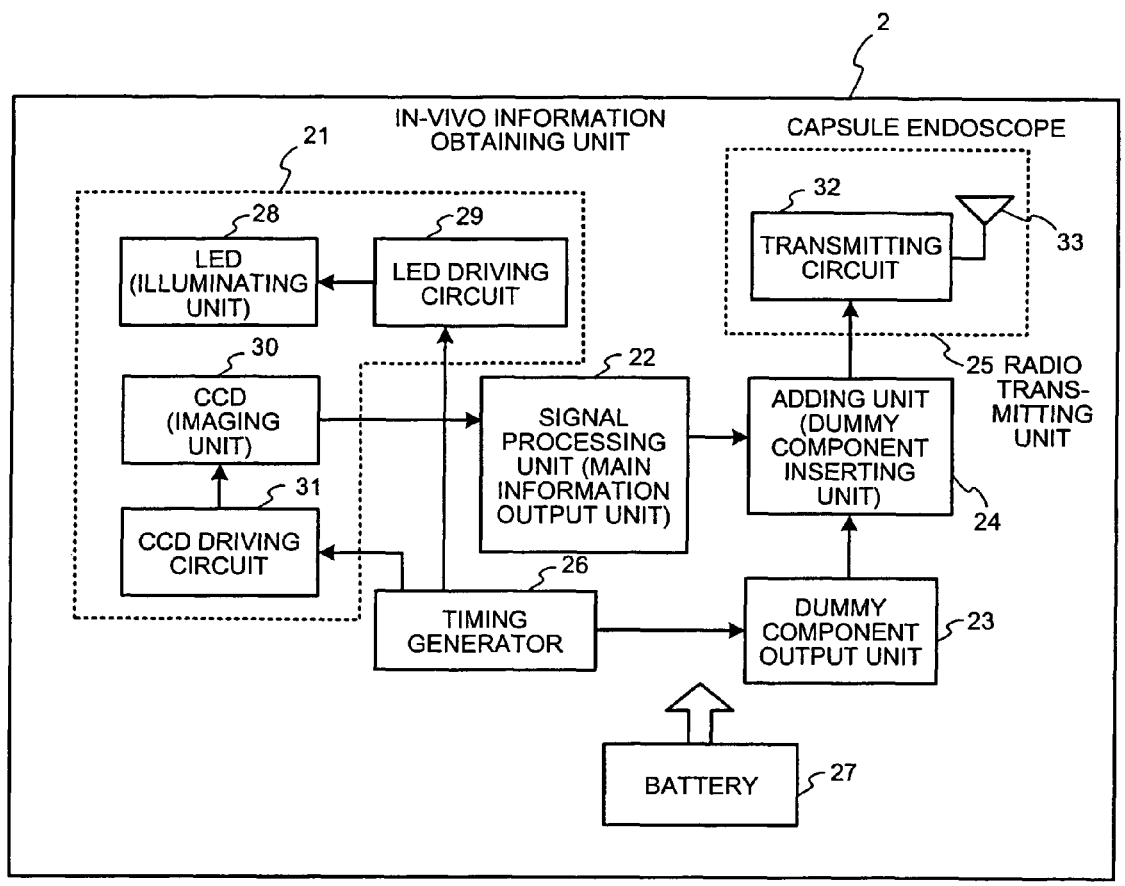
FIG. 3 is a block diagram of a structure of a capsule endoscope included in the body-insertable apparatus system.

FIG. 3 is a block diagram of a schematic structure of the capsule endoscope 2. As shown in FIG. 3, the capsule endoscope 2 has an in-vivo information obtaining unit 21 that serves to obtain in-vivo information, and a radio transmitting unit 25 that serves to transmit the obtained in-vivo information to the receiving apparatus 3 by radio. Further, the capsule endoscope 2 includes a signal processing unit 22 that performs a predetermined process on the in-vivo information supplied from the in-vivo information obtaining unit 21 and outputs a main information portion, a dummy component output unit 23 that generates and outputs a dummy component which is an alternating-current signal, and an adding unit 24 that combines the main information portion and the dummy component and outputs the result to the radio transmitting unit 25. The capsule endoscope 2 further includes a timing generator 26 that serves to synchronize driving timings of the respective components described above, and a battery 27 that serves to supply driving power to the respective components.

The in-vivo information obtaining unit 21 serves to obtain in-vivo information when the capsule endoscope 2 is introduced inside the subject 1. In the first embodiment, the in-vivo information obtaining unit 21 obtains intra-subject images as the in-vivo information, and includes an imaging mechanism for the obtainment of the images. Specifically, the in-vivo information obtaining unit 21 includes an LED 28 that serves as an illuminating unit, an LED driving circuit 29 that controls driving of the LED 28, a CCD 30 that serves as an imaging unit which images at least a part of a region illuminated by the LED 28, and a CCD driving circuit 31 that controls driving of the CCD 30. In the first embodiment, the CCD is employed as the imaging unit. The imaging unit, however, is not necessarily a CCD, and may include a CMOS or the like, for example.

The radio transmitting unit 25 serves to externally transmit information supplied via the adding unit 24 by radio. Specifically, the radio transmitting unit 25 includes a transmitting circuit 32 that performs a necessary modulation processing or the like on supplied information, and a transmitting antenna 33.

Figure 4:
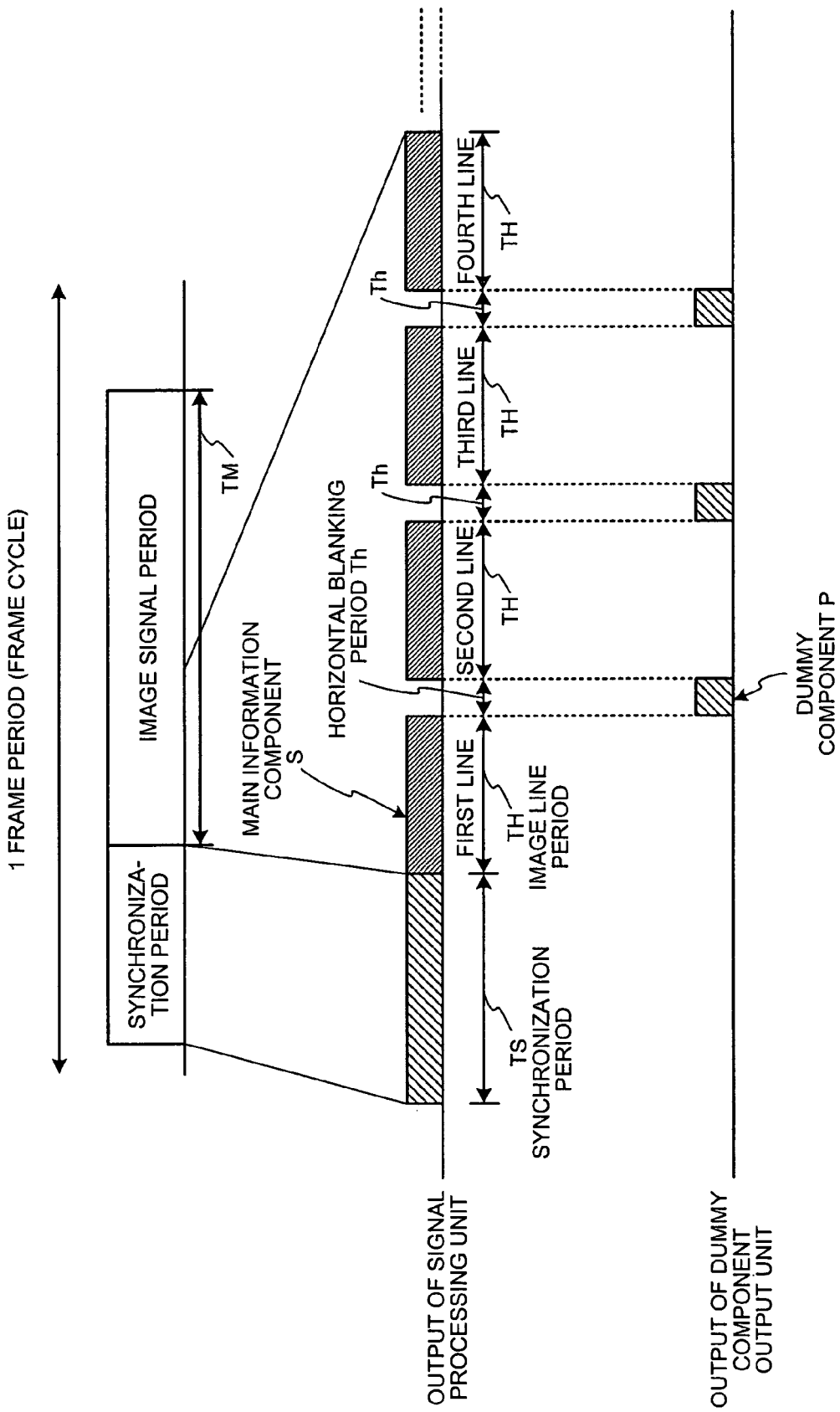
FIG. 4 is a timing chart showing a main information component which is output from a signal processing unit and a dummy component which is output from a dummy component output unit.

The signal processing unit 22 serves to generate image signals by performing a predetermined process on image information obtained by the CCD 30, and corresponds to and functions as a main information output unit as recited in the appended claims. In the first embodiment, the image signal output from the signal processing unit 22 serves as a main information portion as recited in the appended claims. Specifically, the image signals have a structure as shown in FIG. 4, and the signal processing unit 22 outputs signal components that correspond to respective signal lines and that included in the image information obtained by the CCD 30 during an image signal period TM which constitutes one frame period (frame cycle) corresponding to one image frame. In particular, the image signal period TM includes image line periods TH of the number corresponding to the number of the scanning lines, as shown in FIG. 4. The signal processing unit 22 generates and outputs a main information component S which corresponds to each scanning line of the image information in each image line period TH. Here, a horizontal blanking period Th is interposed between the two consecutive image line periods TH. The signal processing unit 22 outputs image signals containing no signal components during the horizontal blanking periods Th.

As shown in FIG. 4, a synchronization period is provided in a first half of one frame period for a synchronization operation. The signal processing unit 22 has a function of generating and outputting a synchronization signal corresponding to the synchronization period TS. The synchronization signal contains information components necessary for the synchronization operation at an extraction of image data from the radio signals received at a receiving apparatus side. In the first embodiment, the synchronization signal is treated as one example of the main information component S.

The dummy component output unit 23 serves to generate and output a dummy component containing alternating-current signals of a predetermined frequency at a predetermined timing. As shown in FIG. 4, the dummy component output unit 23 has a function of outputting a dummy component P corresponding to the horizontal blanking period Th. The dummy component output unit 23 is previously provided with a counter which is in synchronization with horizontal synchronization signals and vertical synchronization signals, for example. The dummy component output unit 23 has a function of generating and outputting the dummy component P using a counter value as the reference.

Figure 5:
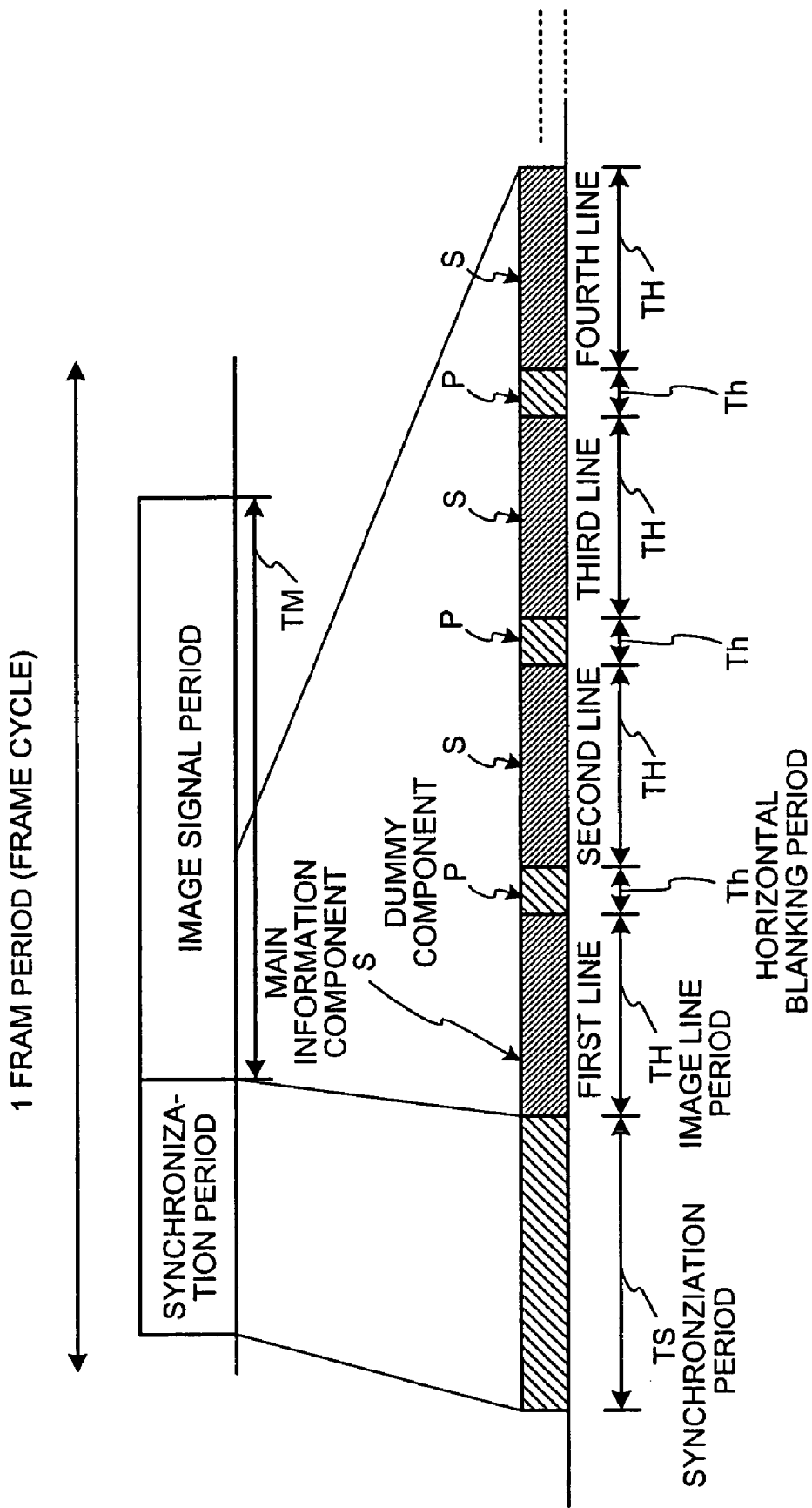
FIG. 5 is a schematic diagram of a specific structure of the dummy component.

The dummy component which is generated and output by the dummy component output unit 23 serves to alleviate an inconvenience in the processing by the receiving apparatus 3. FIG. 5 is a schematic diagram of an example of a structure of the dummy component. As shown in FIG. 5, the dummy component generated and output by the dummy component output unit 23 may be, for example, a pulse signal generated in a single frequency.

An average level and an average frequency of the dummy components P generated and output by the dummy component output unit 23 can be set to an optional value. More preferably, however, when the main information components S contained in a previous stage to the stage of the dummy components S differs from the main information components S contained in a following stage of the stage of the dummy components S in average level, the average level of the dummy components P may be set to an intermediate value of the two average levels, for example an average value of the two average levels. On the other hand, when the main information components S contained in the previous stage to the stage of the dummy components S has the same average level as the average level of the main information components S contained in the following stage of the stage of the dummy components S, the average level of the dummy components P may be set to a value substantially equal to each of the two average levels. Further, when the frequency of the main information components S contained in the previous stage to the dummy components P differs from the frequency of the main information components S contained in the following stage of the dummy components P, the average frequency of the dummy components P is set to a value between the two frequencies, for example, an average value of the two. On the other hand, when the frequency of the main information components S contained in the previous stage to the dummy components P is the same as the frequency of the main information components S contained in the following stage of the dummy components P, the average frequency of the dummy components P is set to a value substantially equal to each of the two frequencies. In an example of FIG. 5, based on the assumption that the average level and the frequency of the respective sets of main information component S do not fluctuate, pulse signals are employed as the dummy components P in such a manner that the average level and the frequency of the dummy components P coincide with the average level and the frequency of the main information components S.

The adding unit 24 functions as an example of a dummy data inserting unit as recited in the appended claims. Specifically, the adding unit 24 has a function of combining the main information component supplied from the signal processing unit 22 and the dummy component supplied from the dummy component output unit 23, and has a function of outputting a combined signal to the transmitting circuit 32.

Figure 6:
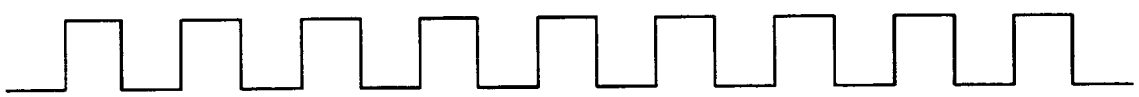
FIG. 6 is a schematic diagram of a structure of a signal component which is output from an adding unit.

FIG. 6 is a schematic diagram of a content of a signal supplied from the adding unit 24. A shown in FIG. 5, the signal output from the adding unit 24 has a structure in which the dummy component P is inserted into a gap portion between the main information portions S that constitute the image signal. Thus, the signal as a whole does not have a gap portion. When such a signal is transmitted from the adding unit 24 to the transmitting circuit 32, the transmitting circuit 32 performs processing such as modulation on the signal shown in FIG. 6, and the processed signal is transmitted by radio via the transmitting antenna 33 to the receiving apparatus 3.

Then, the receiving apparatus 3 receives the radio signals transmitted from the capsule endoscope 2 via the selected receiving antenna 7. After received by the receiving apparatus 3, the radio signals are subjected to the processing such as demodulation by the receiving circuit 11 included in the external device 8, and noise components of the processed radio signals are removed by the frequency filter 12. Thereafter, the AC coupling circuit 13 reproduces the DC components of the radio signals. The resulting radio signals are supplied to the signal processing circuit 14. The signal processing circuit 14 performs a predetermined process and supplies the image signal S1 to the storage unit 16 via the control unit 15. The storage unit 16 stores the content of the image signal S1 in the portable recording medium 5.

An advantage of the body-insertable apparatus system according to the first embodiment will be described. As described above, in the body-insertable apparatus system according to the first embodiment, the radio signals transmitted from the capsule endoscope 2 which serves as the transmitting apparatus has a dummy component inserted into a portion corresponding to the horizontal blanking period. Due to such structure of the radio signal, the body-insertable apparatus system according to the first embodiment has an advantage that a processing cost of the receiving apparatus side is reduced, and that the noise components of the radio signals can be effectively removed during the processing.

In other words, since the dummy component which is an alternating-current signal is inserted into a portion corresponding to the horizontal blanking period in the radio signal, an abrupt voltage change in the radio signal is prevented from occurring at a boundary between a portion corresponding to the image line period and a portion corresponding to the horizontal blanking period in the radio signal transmitted from the capsule endoscope 2. Therefore, when the AC coupling circuit 13 in the external device 8 processes the radio signal to equalize the average level thereof using the AC coupling, the instant voltage change does not exert a negative effect on the processing. Thus, the capsule endoscope 2 is advantageous in that the capsule endoscope 2 can transmit the radio signal in such a manner that the processing cost of the receiving apparatus side is reduced.

To enjoy the above described advantage, any component can be used as the dummy component to be inserted into the gap portion as far as the component is made up of a predetermined alternating-current signal. An insertion of the alternating-current signal as the dummy component can suppress the fluctuation of the average level dissimilar to the conventional technique where a direct-current component corresponding to only one of the logical HIGH and the logical LOW is employed. More preferably, however, the dummy component is at a level substantially equal to the average level of the main information portion, and ideally at a level equal to the average level of the main information portion as described above. Then, the instant voltage changes such as sags can be nearly completely eliminated, and the processing cost at the AC coupling circuit 13 can be further reduced.

Further, the first embodiment has an advantage that the insertion of the dummy component which is an alternating-current signal into the horizontal blanking period can prevent the inclusion of a low-frequency component into the radio signals transmitted from the capsule endoscope 2. When the gap portion is filled up with a direct-current component of only a predetermined voltage corresponding to one of the logical HIGH and the logical LOW as in the conventional system, the radio signal inevitably includes a low-frequency component corresponding to the time length of the gap, such as the horizontal blanking period. Correspondingly, the frequency pass band of the frequency filter 12 provided in the receiving apparatus 3 side becomes wider. Dissimilar to the conventional system, since the system of the first embodiment inserts the dummy component made up of the alternating-current signal into the gap portion, the transmitted radio signal does not include low-frequency component corresponding to the time length of the gap, whereby the transmission of the radio signals, which has a narrower frequency bandwidth than the frequency bandwidth of the conventionally employed signal, is allowed.

Thus, the receiving apparatus 3 that receives the radio signals can set the frequency pass band of the frequency filter 12 provided therein to a narrower range than the conventionally employed range. The narrower frequency pass band is advantageous in that the removal of the noise components can more effectively be performed.

Further, in the first embodiment, the alternating-current signal that constitutes the dummy component is an alternating-current signal of a single clock as shown in FIG. 5. When the dummy component has such a structure, the structure of the dummy component output unit 23 can be simplified. Further, when a separate filtering mechanism, which serves to extract a frequency component corresponding to the frequency of the single clock shown in FIG. 5, is provided, it is possible to readily locate the gap, i.e., the horizontal blanking period in the first embodiment.

The alternating-current signal that constitutes the dummy component may have a structure other than the one shown in FIG. 5. For example, the single clock shown in FIG. 5 may be replaced with a Pseudo Noise (PN) code. The PN code is a generic term referring to spread code sequence employed for spectrum spreading. When the dummy component is made up of such a code sequence, alternating-current signals with a wide range of frequency bandwidth are included in the dummy component. Even when the PN code is employed, the above described advantage can be enjoyed if the average frequency and the average level are set to the same levels as those of the main information portion, for example. The use of the PN code is also advantageous in that a peak value of a modulation spectrum can be decreased at the modulation process by the transmitting circuit 32, to enable the spreading of the spectrum.

A body-insertable apparatus system according to a second embodiment will be described. The body-insertable apparatus system according to the second embodiment includes a switching unit in place of the adding unit 24. The switching unit properly switches signals to be supplied to the transmitting circuit 32 from one to another to insert a dummy component into a gap portion between the main information components.

Figure 7:
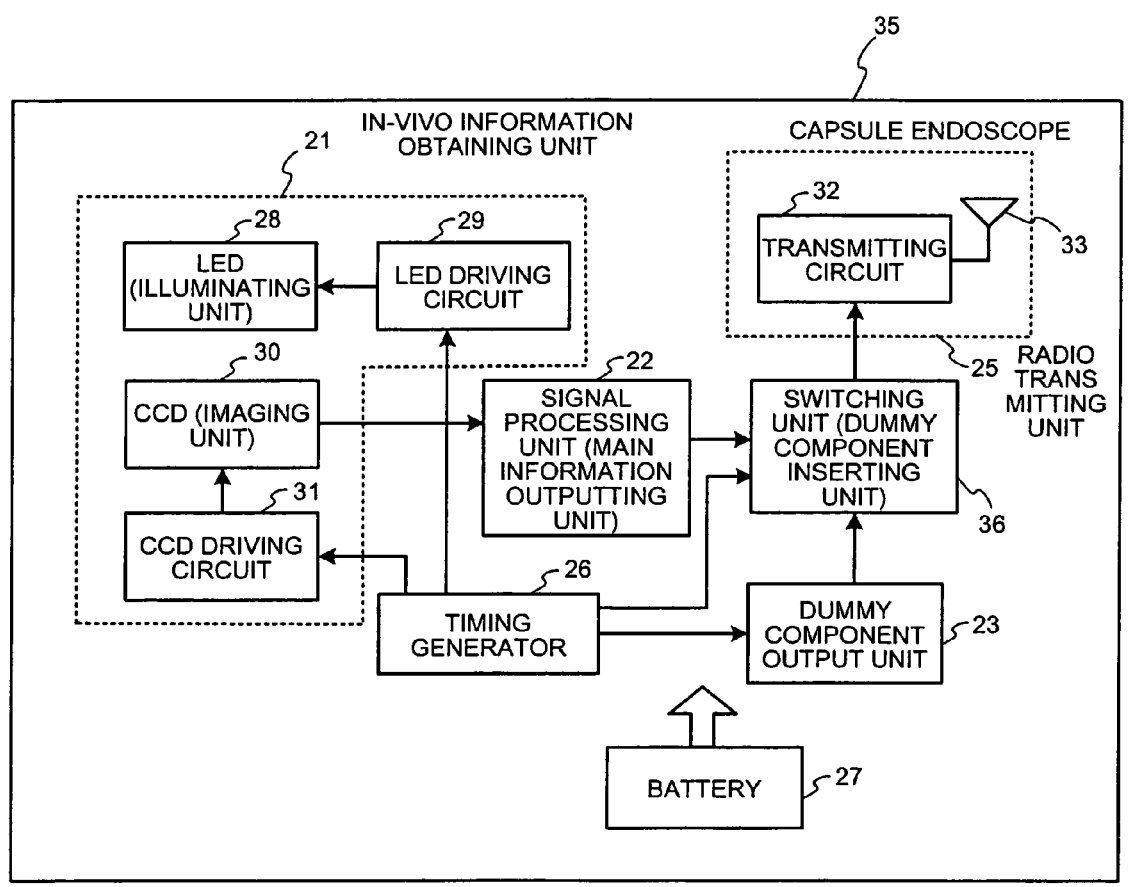
FIG. 7 is a block diagram of a structure of a capsule endoscope included in a body-insertable apparatus system according to a second embodiment.

FIG. 7 is a block diagram schematically showing a structure of a capsule endoscope 35 included in the body-insertable apparatus system according to the second embodiment. As shown in FIG. 7, the capsule endoscope 35 includes a switching unit 36 to which the signal processing unit 22 and the dummy component output unit 23 supply signals. In the second embodiment, the elements denoted by the same reference characters and the same names as those in the first embodiment should be understood to have the same structure and function as those in the first embodiment, if not specified otherwise. The body-insertable apparatus system according to the second embodiment includes the receiving apparatus 3, the display device 4, and the portable recording medium 5, similar to the system of the first embodiment, though not specifically shown in the drawings.

The switching unit 36 has a function of selecting one of the signal components supplied from the signal processing unit 22 and the dummy component output unit 23, to output the selected signal component to the transmitting circuit 32 according to a predetermined timing. Specifically, the switching unit 36 has a function of outputting the main information component supplied from the signal processing unit 22 to the transmitting circuit 32 during the synchronization period and during the image line period in the image signal period, and to output the dummy component supplied from the dummy component output unit 23 to the transmitting circuit 32 during the horizontal blanking period following an operation clock supplied from the timing generator 26.

When the main information component supplied from the signal processing unit 22 is focused in the above operation, the above operation can be regarded as processing of two adjacent main information components where the dummy component is inserted into the gap portion therebetween. In this sense, the switching unit 36 of the second embodiment serves as an example of the dummy component inserting unit as recited in the appended claims. Thus, even when the switching unit 36 is employed in place of the adding unit 24, the same advantage as in the first embodiment can be enjoyed.

When the dummy component is inserted between the main information components by the switching unit 36 as in the second embodiment, the timing of insertion is controlled by the switching unit 36. Therefore, the dummy component output unit 23 may constantly generate and output the dummy component, rather than only during the horizontal blanking period. In the example shown as the second embodiment, however, the dummy component output unit 23 generates and outputs the dummy component only during the horizontal blanking period similarly to the first embodiment, in order to prevent the generation and the outputting of the dummy component from increasing the power consumption.

A body-insertable apparatus system according to a third embodiment will be described. In the third embodiment, the capsule endoscope has a physical structure in which the in-vivo information obtaining unit and the dummy component output unit are formed on different boards, respectively.

Figure 8:
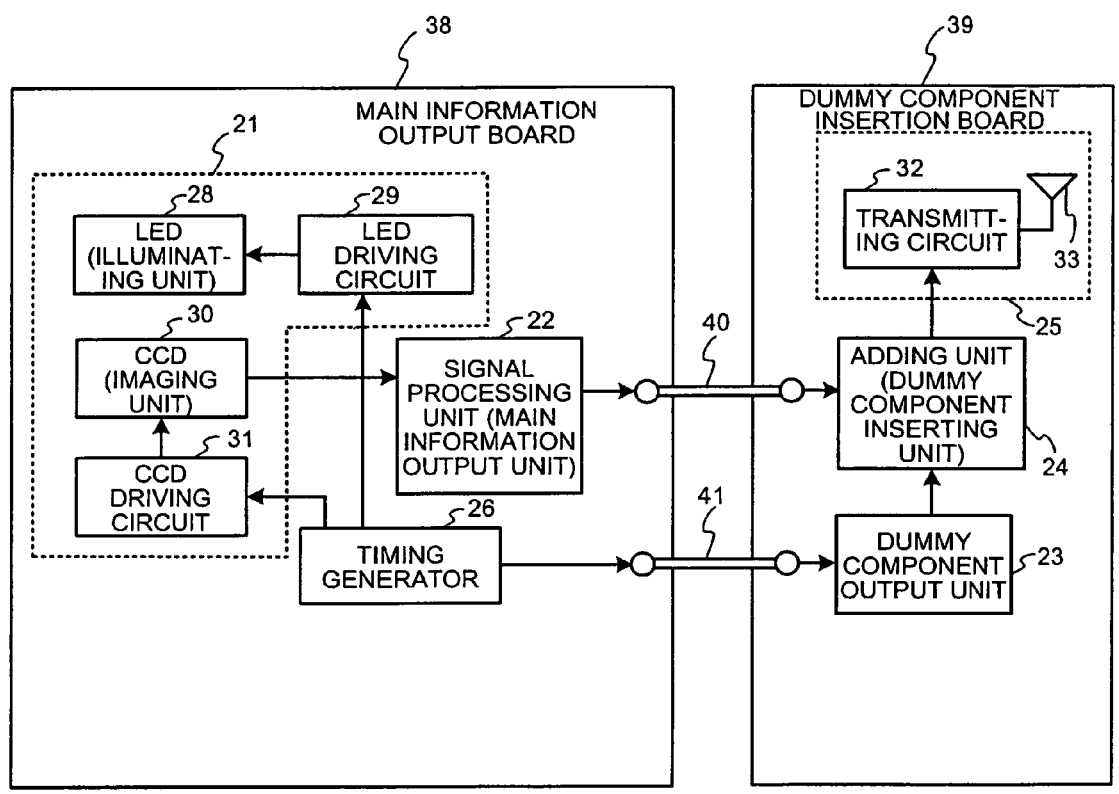
FIG. 8 is a block diagram of a structure of a capsule endoscope included in a body-insertable apparatus system according to a third embodiment.

FIG. 8 is a schematic diagram of a structure of a capsule endoscope included in the body-insertable apparatus system according to the third embodiment. As shown in FIG. 8, in the third embodiment, the in-vivo information obtaining unit 21, the timing generator 26, and the signal processing unit 22 are formed on a main information portion output board 38, whereas the dummy component output unit 23, the adding unit 24, and the radio transmitting unit 25 are formed on a dummy component insertion board 39 which is formed separately from the main information portion output board 38. Wirings 40 and 41 are arranged between the main information portion output board 38 and the dummy component insertion board 39, to electrically connect respective components formed on the boards.

The dummy component output unit 23 has a function of generating a dummy component independently of the information obtained by the in-vivo information obtaining unit 21. When the dummy component output unit 23 and the in-vivo information obtaining unit 21 are formed on the same board, noise components attributable to the operation of the dummy component output unit 23 may be mixed into the image signal due to parasitic capacitance or the like generated between the dummy component output unit 23 and the in-vivo information obtaining unit 21. Particularly, since the in-vivo information obtaining unit 21 performs an imaging operation or the like of a next image even during the horizontal blanking period, the possibility of the influence of the operation of the dummy component output unit 23 cannot completely be denied.

To solve the problem as described above, the third embodiment provides the in-vivo information obtaining unit 21 and the dummy component output unit 23 on separate independent boards, respectively, so as to reduce the possibility of the influence of the operation of one unit to the operation of another to an ignorable level. The body-insertable apparatus system according to the third embodiment, having the above described structure, has an advantage in addition to the advantage of the first embodiment that the in-vivo information obtaining unit 21 can obtain a high-quality intra-subject image.

The first to the third embodiments of the present invention are described above. The present invention, however, should not be limited to the embodiments described above in the interpretation thereof, and those skilled in the art can reach various embodiments and modifications. For example, in the first to the third embodiments, the dummy component is inserted into the gap portion corresponding to the horizontal blanking period. It should be obvious, however, that the dummy component can be inserted into a gap portion other than the one described above. The present invention can exert an effect thereof by inserting the dummy component into any gap portion generated between the main information portions output from the main information output unit, and the gap portion to which the dummy component is inserted into may not be the one corresponding to the horizontal blanking period. Further, the dummy component does not need to be inserted into every gap portion. The dummy component may be inserted into some of the gap portions.

In the first to the third embodiments, information related with the intra-subject image obtained by the in-vivo information obtaining unit 21 is treated as the information contained in the main information portion. The information should not be limited to the one described above, however, and information other than the image information may be processed. Further, the transmitting apparatus to which the present invention is applied does not need to be limited to a capsule endoscope which is a body-insertable apparatus.

A fourth embodiment of the present invention will be described. In the first to the third embodiments described above, the transmitting side inserts the dummy pulse into an image signal at a portion corresponding to the horizontal blanking period or the vertical blanking period, to equalize the average direct-current level of the transmitted signals so that the image signal can be received with a better sensitivity. During the blanking periods, particularly during the horizontal blanking period, data is read out and transferred from a solid-state imaging sensor such as the CCD. When the dummy pulse is inserted into a portion corresponding to the horizontal blanking period, noises of a fixed pattern are sometimes mixed into the image signal, and favorable video information cannot be obtained. The fourth embodiment allows a constant obtainment of video information in a good condition.

Figure 9:
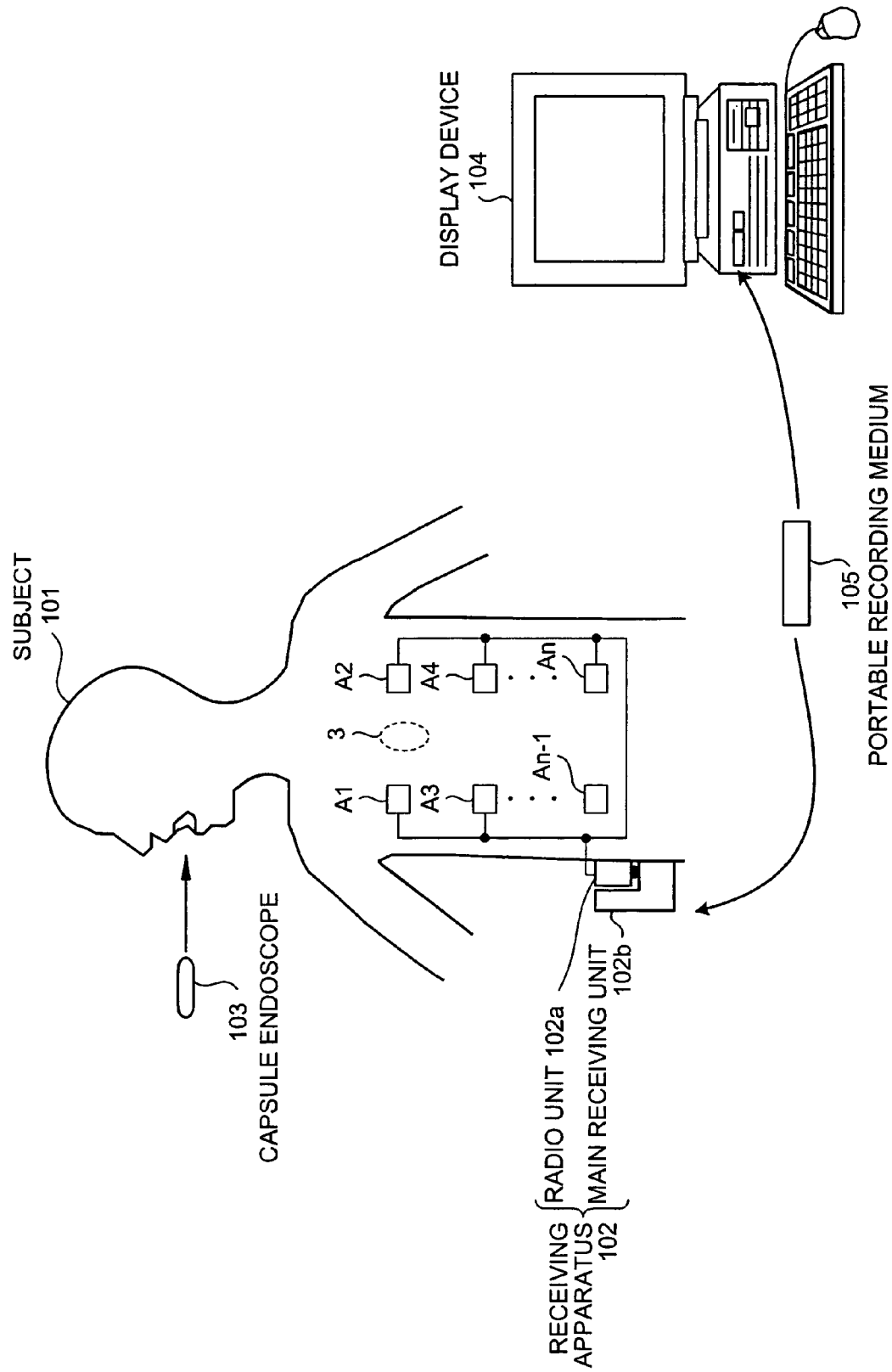
FIG. 9 is a schematic diagram of an overall structure of a wireless in-vivo information obtaining system which includes a capsule endoscope as a transmitting apparatus according to a fourth embodiment of the present invention.

FIG. 9 is a schematic diagram of an overall structure of a wireless in-vivo information obtaining system. The wireless in-vivo information obtaining system employs a capsule endoscope as an example of the body-insertable apparatus. As shown in FIG. 9, the wireless in-vivo information obtaining system includes a capsule endoscope 103 which is inserted inside a subject 101, takes an image inside a body cavity, and transmits data such as an image signal to a receiving apparatus 102, the receiving apparatus 102 which receives image data of inside the body cavity transmitted from the capsule endoscope 103 by radio, a display device 104 which displays an image inside the body cavity based on the image signal received by the receiving apparatus 102, and a portable recording medium 105 which serves for data transfer between the receiving apparatus 102 and the display device 104. The receiving apparatus 102 further includes a radio unit 102a that has plural receiving antennas A1 to An pasted onto an outer body surface of the subject 101, and a main receiving unit 102b that performs, for example, processing of the radio signals received via the plural receiving antennas A1 to An. The radio unit 102a and the main receiving unit 102b are detachably connected to each other via a connector or the like. For example, each of the receiving antennas A1 to An may be provided in a jacket which can be worn by the subject 101, and the subject 101 may wear the jacket so that the receiving antennas A1 to An are indirectly attached to the subject 101. Here, the receiving antennas A1 to An may be detachable from the jacket.

The display device 104 serves to display the image inside the body cavity taken by the capsule endoscope 103. The display device 104 is implemented with a workstation, for example, that displays an image based on data obtained from the portable recording medium 105. Specifically, the display device 104 may directly display the image as in a CRT display, a liquid crystal display, or the like. Alternatively, the display device 104 may output the image onto other media as in a printer, for example.

The portable recording medium 105 is a compact flash (registered trademark) memory, for example, and is detachable from the main receiving unit 102b and the display device 104. The portable recording medium 105 functions so that outputting and recording of information is possible while the portable recording medium 105 is attached to one of the main receiving unit 102b and the display device 104. Specifically, the portable recording medium 105 is attached to the main receiving unit 102b while the capsule endoscope 103 is moving inside the body cavity of the subject 101, and the data transmitted from the capsule endoscope 103 is recorded in the portable recording medium 105. After the capsule endoscope 103 is discharged from the subject 101, i.e., after the imaging inside the subject 101 is finished, the portable recording medium 105 is taken out from the main receiving unit 102b and attached to the display device 104. Then, the data recorded in the portable recording medium 105 is read out by the display device 104. When the data transfer between the main receiving unit 102b and the display device 104 is performed with the portable recording medium 105, the subject 101 can move freely during the imaging inside the body cavity. In addition, such an arrangement contributes to shorten the time required for the data transfer between the display device 104 and the main receiving unit 102b. The data transfer between the main receiving unit 102b and the display device 104 may be performed with other recording device which is embedded inside the main receiving unit 102b, and the main receiving unit 102b and the display device 104 may be connected by a cable or by radio.

Figure 10:
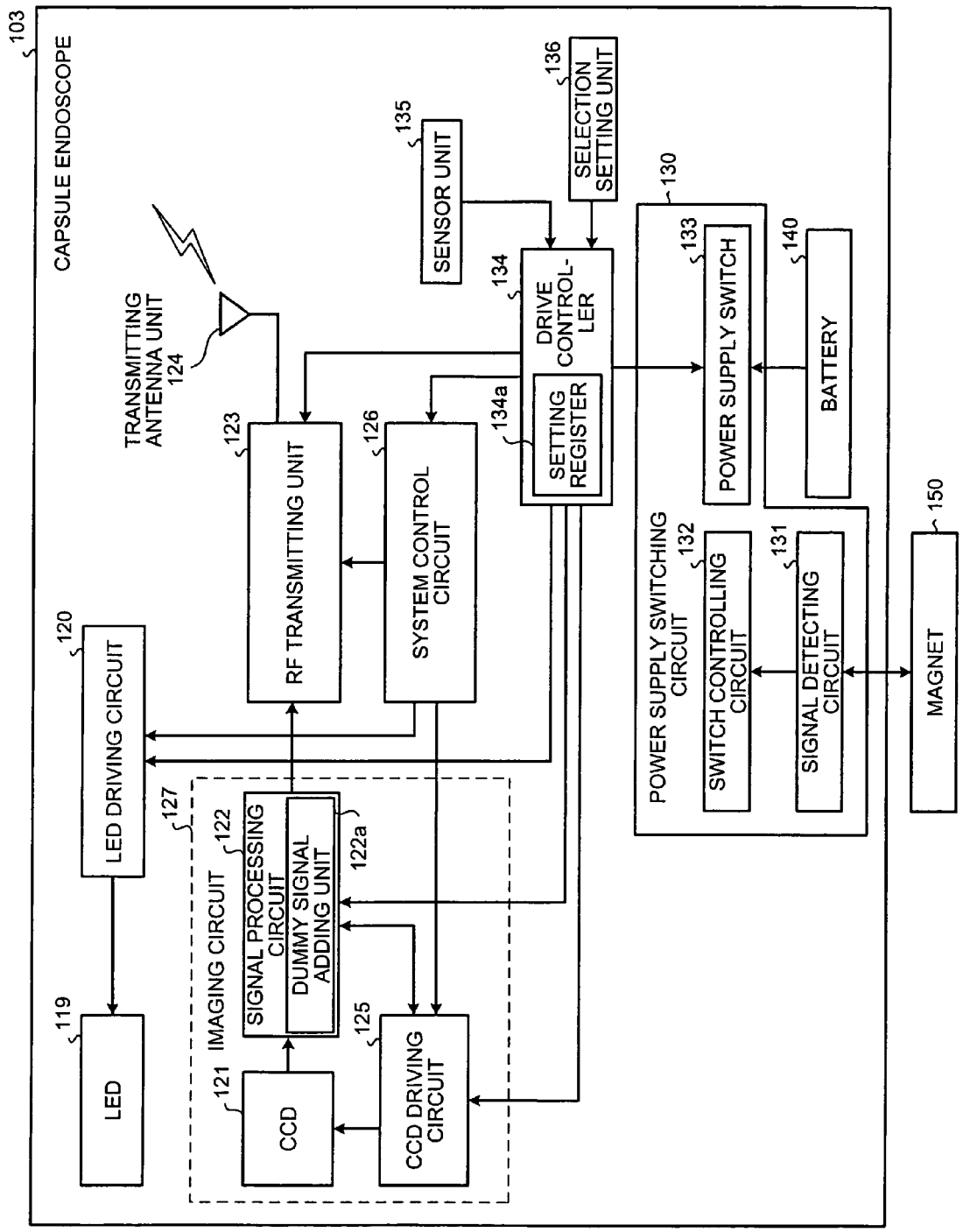
FIG. 10 is a block diagram of a structure of a capsule endoscope shown in FIG. 9.

The capsule endoscope 103 will be described. FIG. 10 is a block diagram schematically showing a structure of the capsule endoscope 103. As shown in FIG. 10, the capsule endoscope 103 includes an LED 119 that illuminates an imaging region when an interior of the subject 101 is imaged, an LED driving circuit 120 that controls a driven state of the LED 119, a CCD 121 that is an imaging element that images a region illuminated by the LED 119, and a signal processing circuit 122 that processes the image signals output from the CCD 121 into imaging information of a desired format. Further, the capsule endoscope 103 includes a CCD driving circuit 125 that controls a driven state of the CCD 121, an RF transmitting unit 123 that modulates image data obtained by the CCD 121 and processed by the signal processing circuit 122, to generate an RF signal, a transmitting antenna unit 124 that transmits the RF signal output from the RF transmitting unit 123, and a system control circuit 126 that controls an operation of each of the LED driving circuit 120, the CCD driving circuit 125, and the RF transmitting unit 123. Here, the CCD 121, the signal processing circuit 122, and the CCD driving circuit 125 are collectively referred to as an imaging circuit 127.

With the above described components, the capsule endoscope 103 illuminates an examined region by the LED 119 and obtains image information of the examined region by the CCD 121 while the capsule endoscope 103 is inside the subject 101. The signal processing circuit 122 processes the obtained image information into image signals. The RF transmitting unit 123 converts the resulting image signals into RF signals. Then, the transmitting antenna unit 124 externally transmits the obtained RF signals.

Further, the capsule endoscope 103 includes a sensor unit 135 that detects predetermined signals such as magnetism, light, and electric waves, and a drive controller 134 that controls driving of the system control circuit 126 which collectively controls processing of the LED driving circuit 120, the CCD driving circuit 125, the RF transmitting unit 123, and the respective components based on the value detected by the sensor unit 135. The sensor unit 135 is implemented with a pH sensor, for example. The sensor unit 135 detects whether the capsule endoscope 103 arrives a predetermined position inside the subject or not, and the drive controller 134 controls the driving of the respective components based on the result of detection. Thus, the power consumption can be suppressed.

Further, the drive controller 134 receives a power supply from a battery 140, which is an energy supply source, via a power switch 133 provided inside a power supply switching circuit 130. The battery 140 is implemented with a button-type battery of silver oxide, for example. The power switch 133 is, in a sense, a main power switch of the capsule endoscope 103. The power switching circuit 130 further includes a signal detecting circuit 131 and a switch controlling circuit 132. The signal detecting circuit 131 serves as an external signal detecting unit that detects a signal coming in from outside the capsule endoscope 103. The signal detecting circuit 131 is implemented with a lead switch, and is turned on and off as a magnet 150 is brought close to and away from the lead switch. Thus, the switch controlling circuit 132 is turned on and off depending on the presence of magnetic influence on the lead switch, and the switch controlling circuit 132 controls the power switch 133 so that the power switch 133 is turned on and off in a toggled manner according to control signals, i.e., on/off signals from the signal detecting circuit 131. The power switch 133 is turned on or off by the magnet 150 before the capsule endoscope 103 is inserted into the subject, so that, for example, performance of the capsule endoscope 103 can be checked.

The signal processing circuit 122 includes a dummy signal adding unit 122a. The dummy signal adding unit 122a adds a dummy pulse to the image signal in a portion corresponding to the vertical blanking period or the horizontal blanking period (hereinafter collectively referred to as blanking period) in synchronization with the horizontal synchronization signal and the vertical synchronization signal of the image signal to equalize the average direct-current level of the transmitted signals.

On the other hand, the drive controller 134 has a setting register 134a. The setting register 134a stores, for example, information on whether the dummy signal adding unit 122a adds the dummy pulse or not, and a content of the dummy pulse if the dummy pulse is added. The contents set in the setting register 134a are stored as plural setting modes. A selection setting unit 136 selects one of the setting modes to set the mode. The drive controller 134 controls the addition of the dummy signal by the dummy adding signal unit 122a according to the setting mode.

FIG. 11 is a diagram showing an example of the set contents in the setting register 134a. As shown in FIG. 11, the setting register 134a stores register values and contents of dummy signal processing in association with each other. The setting register 134a stores eight patterns of dummy signal processing each corresponding to one of the register values"0" to"7". The register value "0" corresponds to a process according to which the dummy signal is not added; the register values"1" to"3" correspond to processes according to which a clock pulse having ½, ¼, and ⅛ the frequency of the imaging clock, which is a reading clock of the CCD 121, is employed as the dummy pulse, respectively; the register values"4" to"6" correspond to processes according to which a clock pulse having ½, ¼, and ⅛ the frequency of the transfer clock of digital data at the signal processing circuit 122 is used as the dummy pulse, respectively; and the register value"7" corresponds to an alternating process alternately adding signals of"on" (high level) and"off" (low level) to consecutive blanking period unit (see FIG. 15) repeatedly.

Figure 12:
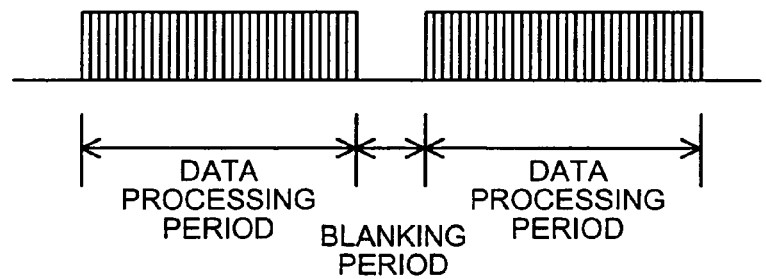
FIG. 12 shows a relation between a data processing period and a blanking period.

Each of the dummy signal processing set by the setting register 134a will be described. As shown in FIG. 12, in the processing of the imaging signal, a one-line data processing period and the blanking period are provided. During the blanking period, pixel signals corresponding to one line are read out from the CCD 121. When the register value"0" is selected and set, no dummy pulse is added to the portion corresponding to the blanking period.

Figure 13:
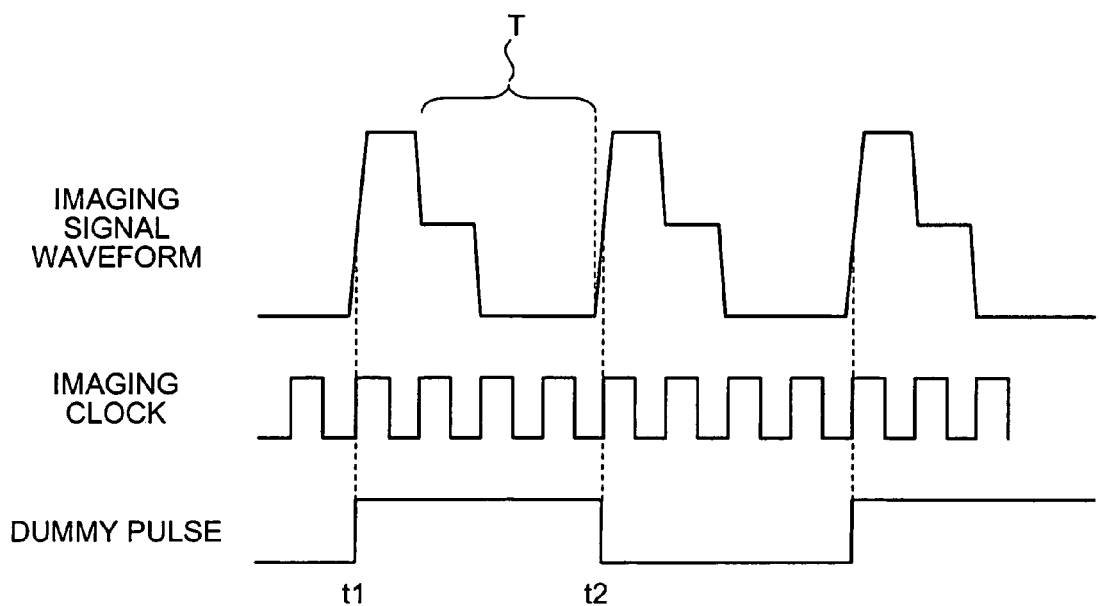
FIG. 13 is a timing chart of dummy pulses generated based on imaging clocks.
Figure 14:
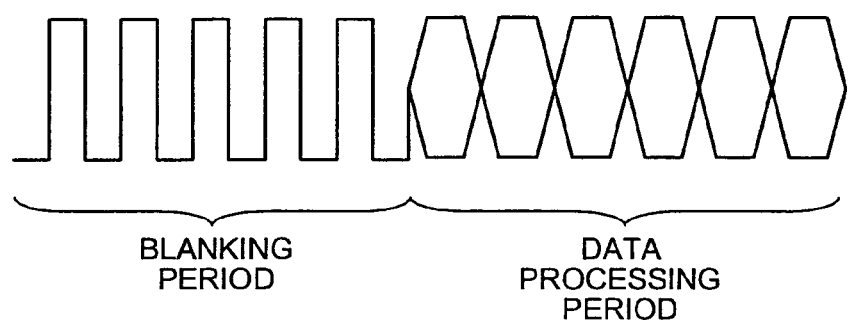
FIG. 14 shows an example of the dummy pulses generated based on transfer clocks for digital processing.

When the register values"1" to"3" are selected, the dummy pulses are generated based on the imaging clock as described above. The dummy pulse has a frequency, which is obtained by dividing the imaging clock by an integer. In FIG. 11, the frequency is set to ½, ¼, and ⅛ that of the imaging clock. The imaging clock is a reading clock of the imaging signals. With the use of the imaging clock, the dummy pulse can be brought into synchronization with the imaging clock. A rising t1 and a falling t2 of the dummy pulse are set to occur during a time period other than an interval T. The imaging signal corresponding to the interval T contains substantial pixel information (see FIG. 13). The noise attributable to the dummy pulse is not mixed substantially into the information of the interval T. Thus, the image information of good quality can be transmitted, and with the addition of the dummy pulses, the average direct-current level can be equalized at the time of reproduction at the receiver side, whereby image information with a good quality can be obtained.

Further, in the process corresponding to the register values"4" to"6", the dummy pulse is a clock obtained by dividing the transfer clock by an integer, as described above. When such a dummy pulse is supplied to the receiver side, the receiver side can generate a timing pulse for fetching data by gradually multiplying the dummy pulse using, for example, a PLL. The dummy pulse contributes to equalize the average direct-current level. At the same time, by effectively using the clock of the dummy pulse, the receiver side can easily generate the timing pulse for fetching data.

Figure 15:
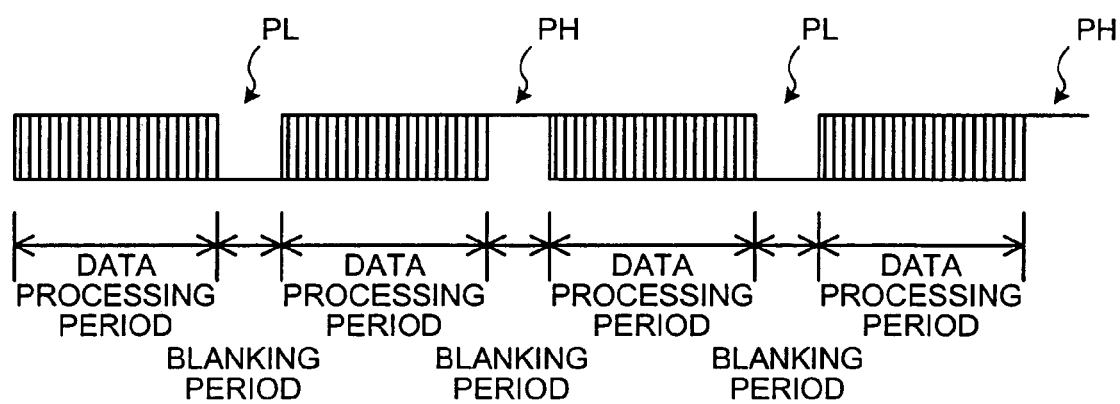
FIG. 15 shows an example of dummy signals in which a high level pulse and a low level pulse each having different polarities are inserted alternately into blanking periods.

Further, when the register value is"7", a high level pulse PH and a low level pulse PL are alternately inserted during the blanking period (see FIG. 15). In other words, the signal assumes an on-state only during the blanking periods to which the pulse PH is inserted. Then, if the receiver side has an AC coupling circuit with a time constant equal to or larger than two lines, the average direct-current level can be made close to the center of amplitude of the cyclic dummy pulse.

The selection setting unit 136 selects one of the setting modes from the setting register 134a which stores the setting modes, i.e., the types of the dummy pulses and whether the dummy pulse is to be added or not. Thus, the dummy pulse can be added flexibly and suitably depending on the receiving apparatus 102 side. When the setting register 134a has the structure as shown in FIG. 11, the selection setting unit 136 can be implemented with a 3-bit DIP switch, for example.

In the fourth embodiment, the setting register 134a is provided on the side of the capsule endoscope 103 which is the transmitting apparatus, and the setting register 134a is made to store plural setting modes concerning the dummy pulse. With the setting of the setting mode by the selection setting unit 135, the dummy pulses can be added selectively, and the addition of various types of dummy pulses can be performed. If the dummy pulse is generated based on the imaging clock and the transitions such as the rising and the falling of the dummy pulse are set to occur in an interval other than the interval corresponding to the substantial pixel signals, the noise does not mix into the image information, and the average direct-current level can be equalized. Further, when the dummy pulse is generated based on the data transfer clock, the clock for data fetching can be easily generated at the receiver side, while the average direct-current level is equalized. Still further, when the pulse whose polarity changes at each blanking period is added, the average direct-current level can be easily equalized without the mixing of noise into the image information.

In the fourth embodiment described above, the capsule endoscope 103 side, i.e., the transmitting apparatus can select one of the plural types of dummy pulses and insert the dummy pulse into the blanking period. In the fifth embodiment, the receiving apparatus 102 side can insert the dummy pulse. The system structure is the same as that of the wireless in-vivo information obtaining system shown in FIG. 9.

Figure 16:
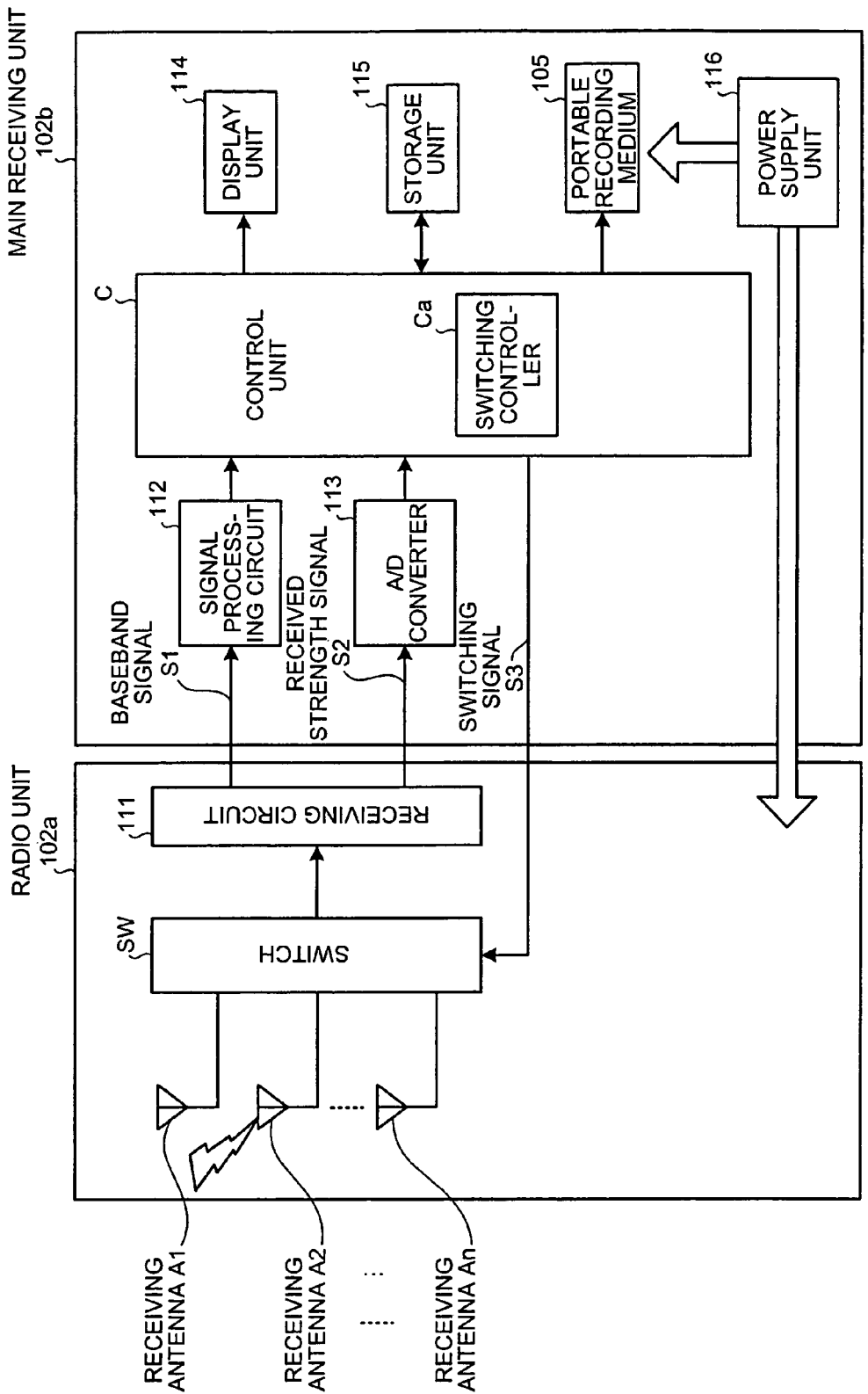
FIG. 16 is a block diagram of a structure of a receiving apparatus.

FIG. 16 is a block diagram of a structure of the receiving apparatus 102 shown in FIG. 9. The radio unit 102a receives the radio signals transmitted from the capsule endoscope 3 and demodulates the same into baseband signals. As shown in FIG. 16, the radio unit 102a includes a changeover switch SW and a receiving circuit 111. The changeover switch SW performs a connection switching process to selectively switch over the receiving antennas A1 to An to select one of the receiving antennas A1 to An. The receiving circuit 111 is connected to a subsequent stage of the changeover switch SW. The receiving circuit 111 amplifies and demodulates the radio signals transmitted from one of the receiving antenna A1 to An that are selectively connected to the receiving circuit 111 via the changeover switch SW.

The main receiving unit 102b receives and processes the baseband signals obtained through demodulation by the radio unit 102a. As shown in FIG. 16, the main receiving unit 102b includes a signal processing circuit 112 which is connected to a subsequent stage of the receiving circuit 111, an A/D converter 113 which is connected to a subsequent stage of the receiving circuit 111, a display unit 114 that displays image data processed by the signal processing circuit 112, a storage unit 115 that stores various types of information, the portable information recording medium 105, a control unit C that controls each of the components, and a power supply unit 116 that supplies power to the main receiving unit 102b and the radio unit 102a. The control unit C has a switching controller Ca that controls the switching of the antennas.

The receiving circuit 111 amplifies the radio signals output from the changeover switch SW and demodulates the amplified radio signals. The resulting signal is a baseband signal S1 which is supplied to the signal processing circuit 112. At the same time, the receiving circuit 111 outputs a received strength signal S2 that indicates the intensity of the amplified radio signal to the A/D converter 113. The signal processing circuit 112 processes the image data. The processed image data is stored in the portable information recording medium 105 under the control of the control unit C, and if necessary, a corresponding image is displayed on the display unit 114. The received strength signal S2 is converted into a digital signal by the A/D converter 113, and the resulting digital signal is taken into the control unit C. The received strength signal S2 is obtained for each of the receiving antennas A1 to An by sequential switching. Based on the received strength signals S2, the switching controller Ca selects a receiving antenna which receives the signal with the highest intensity to use the same to obtain the image data. At the same time, the switching controller Ca outputs a switching signal S3 to the changeover switch SW to give command to switch over to the selected receiving antenna. Further, the control unit C stores the intensities of the signals received by the respective receiving antennas together with the image data in association with the selected receiving antenna in the portable information recording medium 105. The stored values of the intensities of the signals received at the receiving antennas are utilized to calculate an intra-subject position where the capsule endoscope 103 is located when the receiving apparatus 102 receives the image data.

Figure 17:
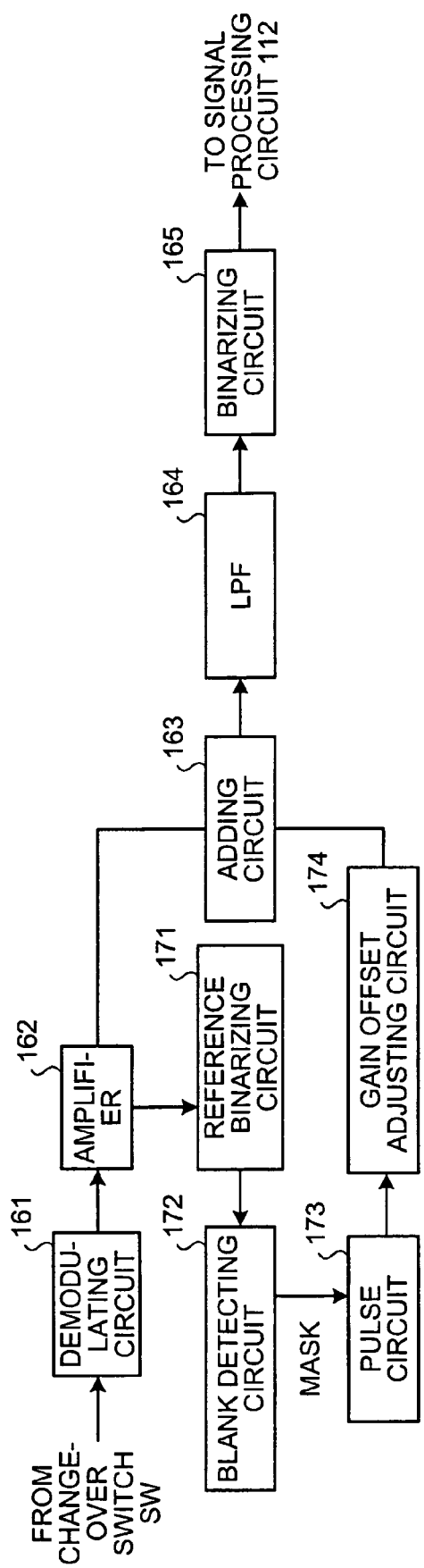
FIG. 17 is a block diagram of a structure of a receiving circuit shown in FIG. 16.

FIG. 17 is a block diagram of a detailed structure of the receiving circuit 111. As shown in FIG. 17, the radio signal supplied from the changeover switch SW is supplied to a demodulating circuit 161, and down-converted to an analog baseband signal, which is further amplified by an amplifier 162, and the amplified signal is supplied to an adding circuit 163.

On the other hand, a reference binarizing circuit 171 receives a branch input of the analog baseband signal from the amplifier 162 to generate a digital baseband signal and supplies the resulting digital baseband signal to a blank detecting circuit 172. The blank detecting circuit 172 detects the blanking period based on the supplied baseband signal and outputs a signal to instruct masking of an interval other than the blanking period to a pulse circuit 173. The pulse circuit 173 generates a pulse signal which is a basis of the dummy pulse, and outputs the dummy pulse in an interval other than the masked interval as instructed by the blank detecting circuit 172. A gain offset adjusting circuit 174 adjusts gain and offset of the dummy pulse so that the dummy pulse supplied from the pulse circuit 173 is adoptable for the baseband signal supplied from the amplifier 162 to the adding circuit 163, and outputs the adjusted dummy pulse to the adding circuit 163.

The adding circuit 163 adds the analog dummy pulse supplied from the gain offset adjusting circuit 174 to the analog baseband signal supplied from the amplifier 162, and outputs the resulting signal to a low pass filter (LPF) 164. As a result, the signals output from the LPF 164 include the dummy pulse inserted into all the portions corresponding to the blanking periods. The baseband signals in which the dummy pulses are inserted are converted into digital signals by a binarizing circuit 165 and the result is output to the signal processing circuit 112. Since all the signals include the dummy pulses in the portions corresponding to all the blanking periods, at the signal processing circuit 112, the average direct-current level is equalized and good image information can be obtained.

A modified example of the fifth embodiment will be described below. In the receiving circuit 111 shown in FIG. 17, the dummy pulse is inserted into every blanking period with the use of the masking process and the adding circuit 163. In the modified example, the dummy pulses are inserted into all the blanking periods with the use of a switch.

Figure 18:
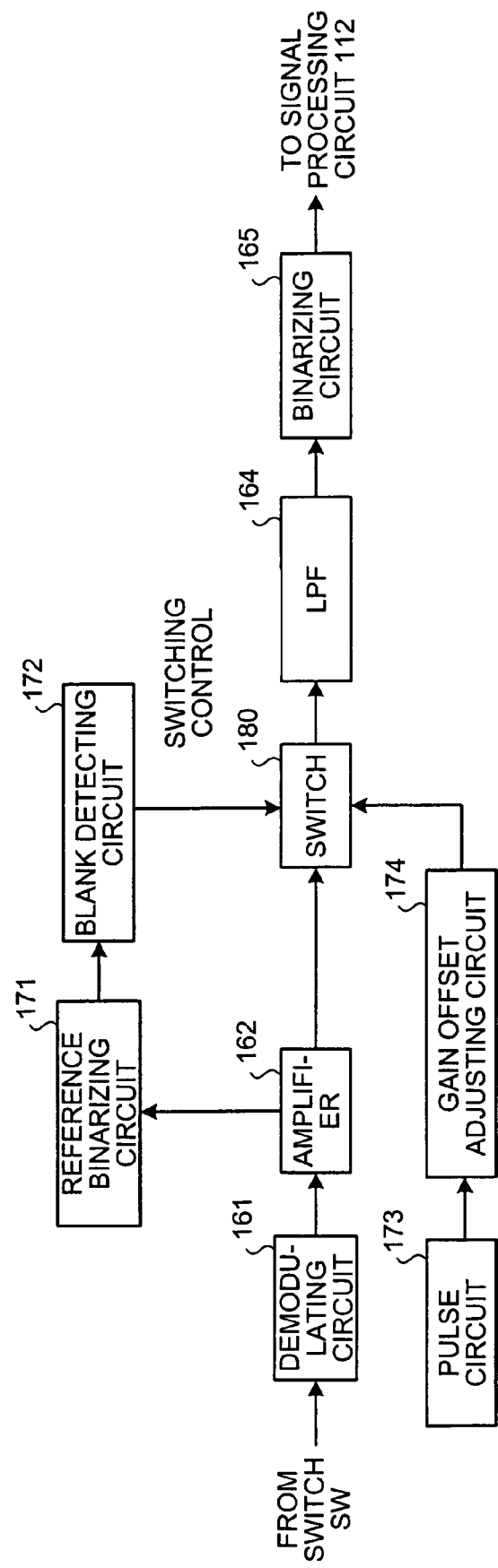
FIG. 18 is a block diagram of a structure of a modified example of the receiving circuit.

FIG. 18 is a block diagram of a detailed structure of the receiving circuit 111 according to the modified example of the fifth embodiment. As shown in FIG. 18, the radio signal supplied from the changeover switch SW is input into the demodulating circuit 161, and down-converted into an analog baseband signal. After the amplification in the amplifier 162, the resulting signal is supplied to a switch 180.

On the other hand, the reference binarizing circuit 171 receives a branch input of the analog baseband signal from the amplifier 162 to generate a digital baseband signal, and outputs the resulting signal to a blank detecting circuit 172. The blank detecting circuit 172 detects the blanking period based on the supplied baseband signal and performs a control to operate the switch 180 according to the presence/absence of the blanking period. Here, the pulse circuit 173 generates a pulse signal as a source of the dummy pulse, and outputs the pulse signal to the gain offset adjusting circuit 174. The gain offset adjusting circuit 174 outputs the dummy pulse supplied from the pulse circuit 173 to the switch circuit 180.

When the blanking period is not detected, the switch 180 outputs the baseband signal supplied from the amplifier 162 to the LPF 164, whereas when the blanking period is detected, the switch 180 outputs the dummy pulse supplied from the gain offset adjusting circuit 174 to the LPF 164. Thus, the switch 180 performs the switching control.

The baseband signal output from the LPF 164 includes the dummy pulse in every portion corresponding to the blanking period. The baseband signal with the dummy pulses inserted is converted into a digital signal by the binarizing circuit 165 and the resulting digital signal is supplied to the signal processing circuit 112. Since the signal include the dummy pulse in every portion corresponding to the blanking period, at the signal processing circuit 112, the average direct-current level is equalized and good image information can be obtained.

In the fifth embodiment, even when the transmitting side does not add the dummy signals corresponding to the blanking periods, the receiving side can add the dummy signals corresponding to all the blanking periods. Therefore, the average direct-current level can be surely equalized in various types of received signals, whereby good image information can always be obtained.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A body-insertable apparatus system, comprising:
a body-insertable apparatus that is inserted into a subject to obtain in-vivo information and that externally transmits an image signal containing the in-vivo information obtained; and
a receiving apparatus that receives the image signal transmitted from the body-insertable apparatus,
the body-insertable apparatus including
a main information output unit that outputs a signal containing a main information portion that contains the obtained in-vivo information, and
a radio transmitting unit that externally transmits the image signal which contains the main information portion, by radio, the receiving apparatus including
- a detecting unit that detects a horizontal blanking period or a vertical blanking period of the image signal; and
- an adding unit that adds a dummy signal which has an average direct-current level of transmitted signals for the blanking period.

2. The body-insertable apparatus system according to claim 1, wherein
the adding unit includes
- a dummy signal generator that generates the dummy signal, and
- a switching unit that outputs the dummy signal supplied from the dummy signal generator as the image signal during the blanking period detected by the detecting unit by switching.

3. The body-insertable apparatus system according to claim 1, wherein
the adding unit includes
- a dummy signal generator that generates the dummy signal, and
- an adding unit that adds the dummy signal supplied from the dummy signal generator to the image signal during the blanking period detected by the detecting unit and outputs a resulting signal.

* * * * *

UNITED STATES PATENT AND TRADEMARK OFFICE
CERTIFICATE OF CORRECTION

PATENT NO. : 7,931,585 B2  
APPLICATION NO. : 11/595051  
DATED : April 26, 2011  
INVENTOR(S) : Seiichiro Kimoto Page 1 of 1

It is certified that error appears in the above-identified patent and that said Letters Patent is hereby corrected as shown below:

On the Title Page:

Related U.S. Application Data should read

Item (63) Continuation of application No. PCT/JP2005/008534, filed on May 10, 2005.

Signed and Sealed this
Twenty-first Day of June, 2011

David J. Kappos
*Director of the United States Patent and Trademark Office*